United States Patent [19]

Miles

[11] Patent Number: 5,260,334
[45] Date of Patent: Nov. 9, 1993

[54] THERMALLY STABILIZED BIS ALKYLTHIO-ALKYLAMINO-N-ALKYL CARBAMATES

[75] Inventor: David L. Miles, Chapel Hill, N.C.

[73] Assignee: Rhone-Poulenc AG Company, Research Triangle Park, N.C.

[21] Appl. No.: 917,452

[22] Filed: Jul. 21, 1992

Related U.S. Application Data

[63] Continuation of Ser. No. 587,543, Sep. 21, 1990, Pat. No. 5,157,050.

[51] Int. Cl.⁵ .................... C07C 331/00; A61K 31/21
[52] U.S. Cl. ........................................ 514/508; 558/3
[58] Field of Search ............................ 514/508; 558/3

[56] References Cited

U.S. PATENT DOCUMENTS 4,297,370  10/1981  Soboczenski ..................... 558/3

Primary Examiner—Johann Richter
Attorney, Agent, or Firm—Morgan & Finnegan

[57] ABSTRACT

Sulfur-linked bis alkylthio alkylamino N-alkyl carbamate pesticides can be stabilized against thermal decomposition induced and accelerated by a variety of contaminants. Thermally stable wettable powder, dispersible granular and liquid formulations of these pesticides can be prepared.

4 Claims, No Drawings

THERMALLY STABILIZED BIS ALKYLTHIO-ALKYLAMINO-N-ALKYL CARBAMATES

This is a continuation of co-pending application Ser. No. 07/587,543 filed Sep. 21, 1990 now U.S. Pat. No. 5,157,050.

FIELD OF THE INVENTION

This invention relates to thermal stabilization of alkylthio-alkylimino carbamate pesticides. More particularly, it relates to the retardation or prevention of thermal decomposition of sulfur-linked bis alkylthio-alkylimino carbamates by incorporation of multioxygen inorganic compounds into formulations containing these pesticides.

BACKGROUND OF THE INVENTION

Sulfur-linked bis alkylthio alkylimino-N-alkyl carbamate pesticides of the formula

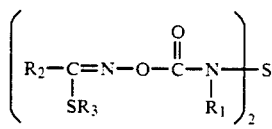

have a wide range of uses in controlling insects and other agronomic pests. Active compounds exhibit a very high level of pesticidal activity and substantially reduced mammalian toxicity and phytotoxicity when compared to other pesticidal compounds having a comparable spectrum of activity against the above mentioned pests.

These compounds are thermally unstable in the presence of a variety of contaminants. Heavy metals and their salts, particularly chloride salts, are especially undesirable. Decomposition is extremely severe in the presence of copper metal, copper chlorides, iron metal, iron chlorides and iron oxide in the form of rust. Other problematic metals include cobalt, nickel and aluminum. Concentrations of as little as 10 ppm are effective if given enough time at temperatures of 60° C. or higher. Sulfur and sulfide salts can also induce decomposition, although usually at rates slower than those of chloride-containing systems. Some organic decomposition initiators have also been identified, including pyridine, pyridine hydrochloride, di- and trisulfides, amines, peroxides and acids (e.g. acetic and citric acids). Presence of 5% or more methomyl or its oxime can also induce decomposition.

The principal object of this invention to provide a method to inhibit or retard the thermal decomposition processes that may occur in bulk quantities of sulfur-linked bis alkylthio-alkylamino-N-alkyl pesticides when they are dried at elevated temperatures or stored for extended periods of time, especially in warmer climates. It is a further object to provide stable wettable powders and dispersible granular formulations of these pesticides.

DETAILED DESCRIPTION OF THE INVENTION

This invention provides a method of retarding or inhibiting thermal decomposition of pesticides of the formula

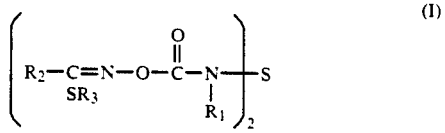

wherein $R_1$ is alkyl containing from one to five carbon atoms; $R_2$ is alkyl, alkylthio, alkoxy, alkanoyl or alkoxycarbonyl, all of which may contain from one to five carbon atoms and which may be unsubstituted or aliphatically substituted in any combination with one or more cyano, nitro, alkylthio, alkylsulfinyl, alkylsulfonyl, alkoxy or $R_4R_5$—NCO— groups; or $R_2$ is phenyl, $R_4R_5$—NCO— or $R_6CON(R_4)$, wherein $R_4$ and $R_5$ are individually hydrogen or alkyl, $R_6$ is hydrogen, alkyl or alkoxy; and $R_3$ is hydrogen, cyano, alkyl or alkylthio containing from one to five carbon atoms; provided that the total number of carbon atoms in $R_2$ and $R_3$ may not exceed eight and provided further that when $R_2$ is alkyl substituted with alkylthio, $R_3$ is alkyl, the inhibition or retardation of thermal decomposition of this compound being achieved by mixing the pesticide with from about 0.01% to about 95% by weight of a substantially non-alkaline inorganic compound containing at least two oxygen atoms bound to a multivalent cationic atom.

This invention also provides a pesticidal composition which comprises: (a) a pesticidally effective amount of a pesticide compound of the formula set forth above and (b) a substantially non-alkaline inorganic compound containing at least two oxygen atoms bound to a multivalent cationic atom, in an amount effective to retard or inhibit thermal decomposition of said compound.

A. Definitions

The term "powdered or granular composition" embraces all solid formulations which range in size from fine dusts (e.g., those which pass through U.S. Sieve screens No. 400 up to No. 100) to substantial particles as large as 5 mm in their largest dimension (e.g. those which pass through a No. 4 U.S. Sieve screen).

A "substantially non-alkaline inorganic compound" is one which, when dissolved or dispersed in water in an amount useful to this invention, does not create a pH greater than 9 or which can be buffered to a pH less than 9.

"Thiodicarb" is the generic name of a pesticide having the formula set forth below:

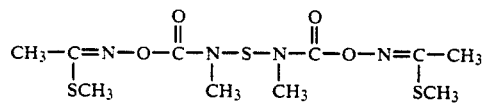

The term "compatability agent" encompasses additives that permit different pesticides to be combined in a single liquid formulation. Such agents may be incorporated into solid or liquid compositions containing one or all of the pesticides to be combined.

B. Pesticides

The organic compounds of this invention are alkylthio-alkylimino-N-alkyl carbamates. They are widely used to control a variety of insect pests. They may be prepared by well known methods, such as those set forth in U.S. Pat. Nos. 4,004,031 and 4,382,957.

In the preferred compounds of this invention $R_1$ and $R_3$ or alkyl and $R_2$ is alkyl or alkylthio. The compound thiodicarb is especially preferred for the practice of this invention.

C. Thermodynamic Stability

Typical decomposition times for thiocarb in the presence of a variety of contaminants are shown in Table I. These data were collected using the following procedure. A one-gram sample of thiodicarb was intimately mixed with the indicated weight percent of contaminant. The solid was placed in a test tube that was then covered with a rubber septum cap and immersed in a constant temperature bath maintained at 100° C. An uncontaminated standard was run under similar conditions. Decomposition was manifested in a variety of forms. Some samples exhibited a rapid change from solid to dark liquid; dense yellow smoke was usually observed. Others underwent gradual discoloration and moistening. In these experiments the time of decomposition was the point when the sample was a dark-brown semi-solid. Reported values were averages of several repetitions for each sample.

The destabilizing effect of methomyl and other sulfur compounds is apparent from Section B of Table I.

TABLE I
STABILITY OF CONTAMINATED THIODICARB STORED AT 100° C.

| Identity Contaminant | Amount of Contaminant | Time to Thiodicarb Decomposition at 100° C. |
|---|---|---|
| A. Standard | | |
| — | | 12-13 days |
| B. Autocatalytic Products | | |
| Methomyl | 1% | 13 days |
| | 5% | 10 days |
| | 10% | 7 days |
| Methomyl oxime | 5% | 3 days |
| | 10% | 7 hours |
| Methyltrisulfide | 1% | 8 days |
| | 3% | 6 days |
| Dimethyl disulfide | 1-3% | 10 days |
| C. Miscellaneous Impurities | | |
| $CuCl_2$ | 2 ppm | 8-9 days |
| | 2% | 5 mins. |
| $FeCl_3$ | 3-300 ppm | 8-9 days |
| | 3% | 10 mins. |
| | 10% | 45 sec. |
| Benzoyl peroxide | 1% | 5 days |
| | 3% | 3-5 days |
| Citric acid | 1-3% | 2 days |
| Acetic acid | 1% | 4-6 days |
| | 3% | 2 days |
| 2-Ethylhexanoic acid | 1-3% | 6-10 days |
| Pyridine | 1-3% | 1-3 days |

Thiodicarb is stable at low concentrations (1% by weight or less) of one of its principal decomposition products, methomyl. However, as the concentration of methomyl is raised, the rate of decomposition increases significantly. Likewise, the effect of methomyl oxime is also substantial. As amounts of other decomposition products, such as dimethyltrisulfide and dimethyldisulfide increase, the rate of decomposition is substantially accelerated.

In Section C of Table I are included results of studies using contaminants that might be introduced during the preparation or storage of the pesticidal substance. As mentioned previously, heavy metal ions, particularly copper and iron, are especially deleterious. Use of manufacturing equipment or storage containers made of these metals in forms that can corrode to produce deleterious salts should be avoided if at all possible. The other organic materials are included to demonstrate the effects that such compounds might have on the product if they should be present, e.g. because they are found in the solvents that are used in the manufacturing process.

The ability of certain silicon-based carriers to reverse the decomposition of contaminated thiocarb is apparent from Table II. In these experiments one-gram samples of thiodicarb were first contaminated with the indicated weight percents of cupric and ferric chloride and then intimately mixed with a variety of silicas and silicates. The samples were then placed in test tubes and immersed in water baths at 50° C., 70° C. and 100° C. until decomposition was observed; decomposition time was measured when the solid had turned into a dark brown liquid. All values represented averages of several repetitions. In some instances stabilization of several orders of magnitude was observed relative to standards containing no silica.

TABLE II
THIODICARB STABILIZATION BY SILICA-BASED CARRIERS

| Contaminant | Stabilizer | Time to Decomposition at | | |
|---|---|---|---|---|
| | | 50° C. | 70° C. | 100° C. |
| — | — | >20 days | 12 days | 11-27 hrs. |
| 1% $CuCl_2$ | — | — | 4 mins. | — |
| 1% $CuCl_2$ | 10% Barden clay | — | >19 hrs. | — |
| 1% $CuCl_2$ | 10% Celite | — | >22 hrs. | — |
| 1% anh. $FeCl_3$ | — | 13-52 mins. | — | 3 mins. |
| 1% anh. $FeCl_3$ | 5% Hi-Sil | 16-19 days | 7-21 hrs. | 4 mins. |
| 1% anh. $FeCl_3$ | 10% Hi-Sil | >30 days | 30-45 hrs. | 100 mins. |

Thermodynamic instability was more accurately and reproducibly evaluated by detection of an exotherm in a dual thermocouple test conducted as follows. A test mixture was prepared by intimately mixing the pesticide standard and the desired quantity of stabilizer. (The pesticide standard was thiodicarb containing sulfur as a synthesis impurity; no additional contaminants were added.) A thermocouple was placed into two grams of dried sample in a measuring vial. A second thermocouple was placed in the vial one inch above the surface of the mixture. The vial was then placed in a heating block and heated as quickly as possible to 160° C.; the rate of heating was not important as long as it was reproducible and the mixture reached 160° C. before the exotherm occurred for untreated pesticide. The time to exotherm for the mixture was compared to that for an untreated standard, i.e. one containing pesticide alone. Measurements for a single mixture of additive and pesticide were usually taken five to ten times to assure reproducibility. In all cases the pesticide was taken from the same batch to avoid differences in contamination levels that are often observed from one batch to the next. The time to exotherm was directly proportional to the thermal stability of the mixture.

As a group substantially non-alkaline inorganic compounds containing at least two oxygen atoms bound to a multivalent cationic atom are surprisingly effective at retarding or inhibiting the occurrence of the exotherm in sulfur-linked carbamate pesticides such as thiodicarb. Included in this group are the phosphorous acids; alkali metal monobasic phosphates, metaphosphates, sulfites or bisulfites; alkali metal or alkaline earth aluminosilicates (zeolites or molecular sieves); alkali metal bicarbonates; and silicon dioxide in the form of silicas and silicates. The compounds that are especially effective at retarding the exotherm are sodium or potassium monobasic phosphate, sulfite or bisulfite; hexametaphosphate; and phosphoric acid. Mixtures of these compounds are also effective. The abilities of several of the preferred stabilizers to retard the exotherm in thiodicarb as measured in the dual thermocouple test described above are apparent from the results shown in Table III. These results indicate that potassium monobasic phosphate is an especially preferred stabilizer for thiodicarb.

TABLE III
TIME TO EXOTHERM FOR STABILIZED THIODICARB

| Additive | | Time to Exotherm (minutes) |
|---|---|---|
| — | | 54 (standard) |
| 4% | molecular sieves 4A | 91 |
| 1% | $Na_2SO_3$ | 75 |
| 5% | $Na_2SO_3$ | 117 |
| 5% | $NaHSO_3$ | 94 |
| 0.5% | $KH_2PO_4$ | >300 |
| 3% | $Na_2HPO_4$ | 58 |

The decomposition of thiodicarb and the increasing concentration of methomyl have been monitored at 100° C. in the presence of sodium monobasic phosphate (Table IV). Samples of thiodicarb untreated and treated with varying amounts of sodium monobasic phosphate were maintained at 100° c. for several days. They were periodically analyzed by standard HPLC methods for thiodicarb and methomyl. As thiodicarb concentration decreased, methomyl concentration increased. However, the results indicated that as the decomposition process continued, other products formed as well; the sum of the weight percentages of methomyl and thiodicarb became progressively smaller as decomposition proceeded. Increasing amounts of the monobasic phosphate appear to stabilize the thiodicarb as the decomposition reaction proceeds over several days; decomposition products, especially methomyl, accelerate the process. These results also support the hypothesis that bis alkylthio-alkylamino-N-alkyl carbamates undergo an autocatalytic decomposition process involving a number of sulfide species, also catalyze the process.

Stabilization of sulfur-linked bis alkylthio-alkylamino-N-alkyl carbamates may be achieved by incorporating the stabilizers of this invention in amounts ranging from 0.01 to 95 percent by weight of total mixture. Although the concentration of a particular inorganic stabilizer must be evaluated empirically, as a general rule preferred concentrations range from about 0.01 to about 10% by weight in solid formulations and from 0.0001% to about 6% by weight in liquid formulations. When the stabilizer is one of the above mentioned phosphate compounds, stabilization will be observed with as little as 0.01 to 2% by weight. Sulfite stabilizers are effective in the range of 0.1 to 5& by weight.

TABLE IV
THIODICARB DECOMPOSITION AND METHOMYL FORMATION IN THE PRESENCE OF $NaH_2PO_4$ at 100° C.

| Stabilizer | | Day 0 | 1 | 2 | 3 | 4 |
|---|---|---|---|---|---|---|
| — | Thiodicarb % | 93.1 | 44.1 | 28 | — | — |
| | Methomyl % | 0.3 | 12.3 | 12.1 | — | — |
| 0.25% | Thiodicarb % | 93.1 | 82.0 | 78.8 | 54.5 | — |
| $NaH_2PO_4$ | Methomyl % | 0.3 | 2.5 | 5.7 | 12.2 | — |
| 0.5% | Thiodicarb % | 93.1 | 81.7 | 77.6 | 55.7 | 56.0 |

TABLE IV-continued
THIODICARB DECOMPOSITION AND METHOMYL FORMATION IN THE PRESENCE OF $NaH_2PO_4$ at 100° C.

| Stabilizer | | Day 0 | 1 | 2 | 3 | 4 |
|---|---|---|---|---|---|---|
| $NaH_2PO_4$ | Methomyl % | 0.3 | 3.6 | 8.3 | 8.2 | 12.9 |
| 1% | Thiodicarb % | 93.1 | 81.6 | 85.9 | 84.8 | 63.9 |
| $NaH_2PO_4$ | Methomyl | 0.3 | 2.2 | 3.9 | 4.3 | 8.5 |

D. Formulations

The compositions of this invention may be applied as solids or as liquid dispersions or solutions to both field and turf to control pests. Application is by methods readily known to those skilled in the art. Effective amounts range from about 0.05 to about 20 lbs. per acre of active pesticide.

Formulations useful in the practice of this invention are solids, as wettable powders or dispersible granulars, and liquids, as solutions or dispersions. The preferred wettable powders and dispersible granular formulations comprise: (a) from about 1% to about 98% by weight of a bis alkylthio-alkylamino-N-alkyl carbamate pesticide; (b) from about 0.01% to about 10% by weight of a substantially non-alkaline inorganic compound containing at least two oxygen atoms bound to a multivalent cationic atom; (c) from about 0.01% to about 20% by weight of wetting agent; and (d) from about 1% to about 12% by weight dispersant.

Preferred liquid formulations comprise: (a) from about 0.01% to about 75% by weight of a bis alkylthio-alkylamino-N-alkyl carbamate pesticide; (b) from about 0.0001% to about 6% by weight of a substantially non-alkaline inorganic compound containing at least two oxygen atoms bound to a multivalent cationic atom; (c) from about 0.01% to about 20% by weight wetting agent; (d) from 0% to about 10% by weight dispersant; and (e) from about 5% to about 80% by weight inert liquid carrier. Suitable carriers include water, unsubstituted aliphatic and aromatic hydrocarbons or analogues containing, for example, alkyl, halo or hydroxy substituents, fatty acids, and oils, such as linseed and cottonseed oil, derived from natural extracts.

Of the pesticides useful in this invention, the preferred compound is thiodicarb. The preferred oxygen-containing inorganic compounds are phosphoric acid and sodium or potassium monobasic phosphate, metaphosphate, sulfite or bisulfite.

Many wetting agents, anionic, cationic or nonionic, are available for these formulations. Illustrative wetting agents are alkali metal salts of fatty alkyl or alkenyl sulfates or sulfonates containing eight to twenty carbon atoms; alkali metal salts of alkylbenzyl or alkylnaphthyl sulfonates wherein the alkyl chain contains eight to twelve carbon atoms; ethoxylated alkylphenols wherein the alkyl groups contain eight to twelve carbon atoms; dialkylesters of sodium sulfonsuccinic acids wherein the dialkyl groups contain five to ten carbon atoms; or polyalkylene oxide modified dimethypolysiloxane in which the alkylene groups are ethylene or propylene or a mixture of both. Other suitable wetting agents may also be used.

Dispersants are materials which interact with solid ingredients in the formulations and the liquid medium that is used to suspend those solids for purposes of application. They must be soluble in that liquid phase and they usually behave as a binder for the solid powder or granular. Representative dispersants useful in the practice of this invention include starches, alkali metal or alkaline earth salts of lignin sulfonates; and condensates of alkali metal alkylnaphthalene sulfonates and organic compounds containing one to three carbon atoms and at least one oxygen atom, such as the condensate of formaldehyde and sodium naphthalene sulfonic acid.

An additional component particularly useful in the formulation of this invention is an antifoaming agent. It prevents or reduces foam during the preparation of the powder or granulars and during dispersion and application of the composition. It also stabilizes the resulting dispersion and permits more rapid redispersion if coagulation of solids occurs in a dispersion. An especially useful antifoamer is a dialkylpolysiloxane. Particularly effective are dimethylpolysiloxanes formulated as emulsions or pastes. Such additives do not act as stabilizers for the pesticides.

Pesticidal formulations containing multiple pesticides are popular for the obvious reason of convenience—only one application is necessary to deposit all of the actives. While many multiple formulations are easily prepared simply by mixing all of the active ingredients, the formulations of this invention may require the presence of a compatability agent that prevents flocculation in the final solution or dispersion that is applied to the target plants. The presence of an additional, chemically unrelated pesticide such as parathion may destabilize a dispersion prepared for spray application. The preferred compatability agents for these compositions are condensates of alkylene oxide and hydrophobic bases made by condensing an alkylene oxide with an alkylene glycol wherein all aklyl substituents contain from two to four carbon atoms. A particularly effective agent is a paste condensate of ethylene oxide with hydrophobic bases formed by condensing propylene oxide with propylene glycol.

A number of other well known ingredients can be incorporated into the wettable powders and dispersible granulars of this invention as the need arises, provided, of course, that they do not affect the ability of the inorganic compound to stabilize the pesticide or the stability and dispersibility or wettability of the powder or granular. These additives might include buffers, carriers or diluents, dyes, fragrances, humectants, thickeners, biocides and anti-evaporative agents.

The solid compositions of this invention can be prepared by various methods well known in the art, such as pan granulation, fluidized bed mixing and drying, spray drying, intensive mixing agglomeration, extrusion, compaction or pelletizing. For pan granulation and fluidized bed processes, a mixture of dry ingredients is prepared and transferred into the mixing/drying chamber that contains water and any liquid ingredients; the slurry is thoroughly mixed and then dried. Particles are then ground to a desired size. If a spray drying process is used, grinding of the mixture of dry ingredients or of the slurry is preferred.

The various processes yield solids containing a spectrum of particle sizes and moisture contents. A useful product is one which meets the particle size requirements for a particular application, which contains less than 5% by weight water, and preferably less than 2%, and which disperses well in water or oil. For granular compositions good dispersibility is obtained with particles retained on a U.S. Screen No. 100 (149 microns), and optimum particle stability is obtained with less than 2% moisture. Any particles that are too small, too large or too wet can be returned to the manufacturing or drying apparatus and recyled.

Preparation of the liquid compositions of this invention may be accomplished by methods known in the art. Useful dispersion formulations will not separate into liquid and solid phases during extended storage at ambient temperatures. To enhance stability the size of dispersed particles may be reduced by techniques, such as air and wet milling, known in the art.

The following examples are offered to illustrate useful formulations of this invention and to demonstrate the effects of various stabilizers.

EXAMPLE 1

To demonstrate the effect of a phosphate stabilizer in a dispersible granular, the following two formulations were prepared (by mixing ingredients in an aqueous slurry and spray drying to less than 2% water) and their thermal stability compared; (all values are percent by weight of the dry ingredients).

| Formulation A (no thermal stabilizer) | Formulation B (thermal stabilizer) | Ingredient |
| --- | --- | --- |
| 87.4% | 86.8% | thiodicarb |
| 8.6 | 8.6 | dispersant (sodium salt of sulfonated naphthylene formaldehyde condensate) |
| 1.3 | 1.3 | dispersant (starch) |
| 2.5 | 2.5 | wetting agent (sodium salt of sulfonated lauryl acid) |
| 0.2 | 0.2 | buffer (citric acid) |
| — | 0.5 | thermal stabilizer (NaH$_2$PO$_4$) |
| — | 0.2 | antifoamer (dimethylpolysiloxane emulsion) |
| Time to Exotherm | | |
| 46 mins. | >120 mins. | |

It is clear that as little as 0.5% NaH$_2$PO$_4$ greatly enhances the thermal stability of this formulation. Formulation B can be stored for much longer times at elevated temperatures (approximately 45°-55° C.) than Formulation A, and Formulation B is much less likely to decompose during drying than is Formulation A.

EXAMPLE 2

A dispersible granular stabilized with silica was prepared by mixing 86.5% by weight thiodicarb containing approximately 3% silica and 3% sulfur; dispersants (1.5% by weight starch, 6.8% by weight sodium salt of sulfonated naththalene formaldehyde condensate, and 3.0% by weight polyalkylene glycol ether); wetting agent (1.0% by weight dioctyl ester of sodium sulfosuccinic acid); antifoamer (1.0% by weight magnesium stearate); and buffer (0.2% by weight citric acid). In this formulation stabilizer (i.e., silica) content was approximately 2.6% by weight. The mixture was ground to a powder of average particle size less than 10 microns and then transferred to a fluidized bed chamber for mixing with water and subsequent drying.

After screening the product to a range of −12 to +40 mesh (U.S. Sieve size), it had the following characteristics:

| | |
| --- | --- |
| CIPAC suspendibility | 76% |

| | |
|---|---|
| Time to exotherm | 104 minutes |

EXAMPLE 3

A very stable sample containing two stabilizers was prepared by slurrying, in water, the following ingredients (all weight percents are based on added weights of the ingredients except water): 86.1% thiodicarb containing 5% sulfur and 1.0% silica; 10.1% dispersant (sodium salt of sulfonated naphthalene formaldehyde condensate); 2.5% wetting agent (sodium salt of a sulfonated lauryl acid); 0.6% antifoaming emulsifier (dimethylpolysiloxane emulsion); and 0.7% thermal stabilizer (KH$_2$PO$_4$). The slurry is wet ground to pass through a No. 325 screen (U.S. Sieve size) and spray dried to a moisture content of less than 2%. Approximately 95% of the resulting granular has a particle size distribution spanning the narrow range of −14 to +100 mesh (U.S. Sieve size).

The granular within this particle size range exhibits the following characteristics:

| | |
|---|---|
| CIPAC suspendibility | 90% |
| Time to exotherm | >120 minutes |

What is claimed is:

1. A pesticidal composition which comprises:

(a) a pesticidally effective amount from about 1% to about 98% by weight of an organic compound of the formula:

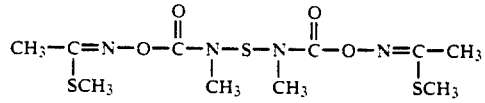

(b) an amount of phosphoric acid from about 0.01% to about 10% by weight or an amount of alkali metal monobasic phosphate salt from about 0.7% to 10% by weight, or a mixture thereof effective to retard or inhibit thermal decomposition of said compound, and (c) said composition is substantially free of water.

2. The pesticidal composition of claim 1 wherein said alkali metal monobasic phosphate salt is potassium or sodium monobasic phosphate.

3. The pesticidal composition of claim 2 which comprises an amount of said organic compound from about 10% to about 95% by weight; said phosphoric acid from about 0.01% to about 1% by weight, or sodium or potassium monobasic phosphate from about 0.7% to about 1.5% by weight, or a mixture thereof; and further comprises a substantially nonaqueous inert solid or liquid carrier from about 0.01% to about 90% by weight; and wetting agents from about 0.01% to about 20% by weight, or dispersants from about 1% to about 12% by weight, or mixtures thereof.

4. The pesticidal composition of claim 1 which comprises an amount of said organic compound from about 10% to about 95% by weight, and an amount of phosphoric acid from about 0.01% to about 10% be weight.

* * * * *